(12) United States Patent
Payne et al.

(10) Patent No.: US 9,636,168 B2
(45) Date of Patent: May 2, 2017

(54) ELECTROSURGICAL INSTRUMENT INCLUDING NESTED KNIFE ASSEMBLY

(71) Applicant: Covidien LP, Mansfield, MA (US)

(72) Inventors: Kellie F. Payne, Rock Hill, SC (US); William H. Nau, Jr., Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 760 days.

(21) Appl. No.: 13/903,223

(22) Filed: May 28, 2013

(65) Prior Publication Data

US 2014/0046323 A1 Feb. 13, 2014

Related U.S. Application Data

(60) Provisional application No. 61/681,425, filed on Aug. 9, 2012.

(51) Int. Cl.
*A61B 18/14* (2006.01)

(52) U.S. Cl.
CPC .. *A61B 18/1445* (2013.01); *A61B 2018/1455* (2013.01)

(58) Field of Classification Search
CPC ........ A61B 18/1445; A61B 2018/1455; A61B 18/14; A61B 18/1442; A61B 18/1448; A61B 18/1455; A61B 18/18
USPC .............................. 606/51, 52, 169, 205–207
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003, 4 pages.

(Continued)

*Primary Examiner* — Michael Peffley
*Assistant Examiner* — Khadijeh Vahdat (57) ABSTRACT

An electrosurgical instrument includes a handle assembly and an end effector assembly operatively coupled with the handle assembly. The end effector assembly includes a first jaw member including a first jaw housing and a first electrically conductive surface, a second jaw member including a second jaw housing and a second electrically conductive surface, and a knife assembly. The knife assembly includes a base member translatably disposed in the first jaw housing, a pivot portion coupled with the base portion, and a blade pivotally associated with the pivot portion. The knife assembly is transitionable between a retracted state in which the blade is disposed within the first jaw housing and an extended state in which the blade is disposed at least partially within the second jaw housing.

3 Claims, 6 Drawing Sheets

(56) References Cited

U.S. PATENT DOCUMENTS

| | | |
|---|---|---|
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,573,534 A | 11/1996 | Stone |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| 5,944,717 A | 8/1999 | Lee et al. |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,752,767 B2 | 6/2004 | Turovskiy et al. |
| D493,888 S | 8/2004 | Reschke |
| D496,997 S | 10/2004 | Dycus et al. |
| D499,181 S | 11/2004 | Dycus et al. |
| 6,840,948 B2 | 1/2005 | Albrecht et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| 7,131,971 B2 | 11/2006 | Dycus et al. |
| D533,274 S | 12/2006 | Visconti et al. |
| D533,942 S | 12/2006 | Kerr et al. |
| 7,150,097 B2 | 12/2006 | Sremcich et al. |
| D535,027 S | 1/2007 | James et al. |
| D538,932 S | 3/2007 | Malik |
| 7,195,631 B2 | 3/2007 | Dumbauld |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,510,556 B2 | 3/2009 | Nguyen et al. |
| 7,540,872 B2 | 6/2009 | Schechter et al. |
| 7,628,791 B2 | 12/2009 | Garrison et al. |
| 7,686,804 B2 | 3/2010 | Johnson et al. |
| 7,695,485 B2 | 4/2010 | Whitman et al. |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,731,717 B2 | 6/2010 | Odom et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,343,151 B2 | 1/2013 | Siebrecht et al. |
| 8,679,140 B2 | 3/2014 | Butcher |
| RE44,834 E | 4/2014 | Dumbauld et al. |
| 8,858,554 B2 | 10/2014 | Kerr et al. |
| 8,920,461 B2 | 12/2014 | Unger et al. |
| 8,939,975 B2 | 1/2015 | Twomey et al. |
| 8,968,298 B2 | 3/2015 | Twomey |
| 8,968,311 B2 | 3/2015 | Allen, IV et al. |
| 8,968,313 B2 | 3/2015 | Larson |
| 9,011,436 B2 | 4/2015 | Garrison |
| 2003/0109802 A1 | 6/2003 | Laeseke et al. |
| 2003/0109875 A1 | 6/2003 | Tetzlaff et al. |
| 2003/0144605 A1 | 7/2003 | Burbank et al. |
| 2005/0203441 A1 | 9/2005 | Voegele |
| 2007/0250242 A1 | 10/2007 | Herges |
| 2008/0058802 A1 | 3/2008 | Couture et al. |
| 2008/0319442 A1 | 12/2008 | Unger et al. |
| 2009/0012520 A1* | 1/2009 | Hixson ............ A61B 18/1445 606/51 |
| 2010/0179543 A1 | 7/2010 | Johnson et al. |
| 2011/0004210 A1 | 1/2011 | Johnson et al. |
| 2012/0095460 A1* | 4/2012 | Rooks et al. ................. 606/45 |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296848 A1 | 11/2013 | Allen, IV et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026 179 | 12/2005 |
| DE | 20 2007 009 318 | 8/2007 |
| DE | 20 2007 009 165 | 10/2007 |
| DE | 20 2007 009 317 | 10/2007 |
| DE | 20 2007 016 233 | 3/2008 |
| DE | 19738457 | 1/2009 |

(56) References Cited

FOREIGN PATENT DOCUMENTS

| DE | 10 2008 018406 | 7/2009 |
|---|---|---|
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 09000538 A | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47149 | 2/1999 |
| JP | 11-47150 | 2/1999 |
| JP | 11-169381 | 6/1999 |
| JP | 11-192238 | 7/1999 |
| JP | 11-244298 | 9/1999 |
| JP | 2000-135222 | 5/2000 |
| JP | 2000-342599 | 12/2000 |
| JP | 2000-350732 | 12/2000 |
| JP | 2001-8944 | 1/2001 |
| JP | 2001-29355 | 2/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 A | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 A | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003, 1 page.
Peterson et al. "Comparison of Healing Process Following Ligation with Sutures and Bipolar Vessel Sealing" Surgical Technology International (2001), 8 page.
"Electrosurgery: A Historical Overview" Innovations in Electrosurgery; Sales/Product Literature; Dec. 31, 2000, 6 pages.
Johnson et al. "Evaluation of a Bipolar Electrothermal Vessel Sealing Device in Hemorrhoidectomy" Sales/Product Literature; Jan. 2004, 1 page.
E. David Crawford "Evaluation of a New Vessel Sealing Device in Urologic Cancer Surgery" Sales/Product Literature 2000, 1 page.
Johnson et al. "Evaluation of the LigaSure Vessel Sealing System in Hemorrhoidectormy" American College of Surgeons (ACS) Clinicla Congress Poster (2000), 1 page.
Carus et al., "Initial Experience With the LigaSure Vessel Sealing System in Abdominal Surgery" Innovations That Work, Jun. 2002, 4 pages.
Heniford et al. "Initial Results with an Electrothermal Bipolar Vessel Sealer" Surgical Endoscopy ,(2001) 15:799-801.
Herman et al., "Laparoscopic Intestinal Resection With the LigaSure Vessel Sealing System: A Case Report"; Innovations That Work, Feb. 2002, 4 pages.
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999, 1 page.
LigaSure Vessel Sealing System, the Seal of Confidence in General, Gynecologic, Urologic, and Laparaoscopic Surgery; Sales/Product Literature; Apr. 2002, 8 pages.
Joseph Ortenberg "LigaSure System Used in Laparoscopic 1st and 2nd Stage Orchiopexy" Innovations That Work, Nov. 2002, 4 pages.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001, 8 pages.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003, pp. 147-151.
"Reducing Needlestick Injuries in the Operating Room" Sales/ Product Literature 2001, 1 page.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001, 1 page.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003, 15 pages.
Dulemba et al. "Use of a Bipolar Electrothermal Vessel Sealer in Laparoscopically Assisted Vaginal Hysterectomy" Sales/Product Literature; Jan. 2004, 1 page.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000, 1 page.
Crawford et al. "Use of the LigaSure Vessel Sealing System in Urologic Cancer Surgery" Grand Rounds in Urology 1999 vol. 1 Issue 4 pp. 10-17.

(56) References Cited

OTHER PUBLICATIONS

Craig Johnson, "Use of the LigaSure Vessel Sealing System in Bloodless Hemorrhoidectomy" Innovations That Work, Mar. 2000, 4 pages.

Levy et al. "Use of a New Energy-based Vessel Ligation Device During Vaginal Hysterectomy" Int'l Federation of Gynecology and Obstetrics (FIGO) World Congress 1999, 1 page.

Barbara Levy, "Use of a New Vessel Ligation Device During Vaginal Hysterectomy" FIGO 2000, Washington, D.C., 1 page.

E. David Crawford "Use of a Novel Vessel Sealing Technology in Management of the Dorsal Veinous Complex" Sales/Product Literature 2000, 1 page.

Jarrett et al., "Use of the LigaSure Vessel Sealing System for Peri-Hilar Vessels in Laparoscopic Nephrectomy" Sales/Product Literature 2000, 1 page.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C., 1 page.

McLellan et al. "Vessel Sealing for Hemostasis During Gynecologic Surgery" Sales/Product Literature 1999, 1 page.

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12:876-878.

Burdette et al. "In Vivo Probe Measurement Technique for Determining Dielectric Properties At VHF Through Microwave Frequencies", IEEE Transactions on Microwave Theory and Techniques vol. MTT-28, No. 4, Apr. 1980 pp. 414-427.

Heniford et al. "Initial Research and Clinical Results with an Electrothermal Bipolar Vessel Sealer" Oct. 1999.

Siegel et al. "The Mechanism of Blood Vessel Closure by High Frequency Electrocoagulation" Surgery Gynecology & Obstetrics, Oct. 1965 pp. 823-831.

Benaron et al., "Optical Time-Of-Flight and Absorbance Imaging of Biologic Media", Science, American Association for the Advancement of Science, Washington, D.C., vol. 259, Mar. 5, 1993, pp. 1463-1466.

Bergdahl et al. "Studies on Coagulation and the Development of an Automatic Computerized Bipolar Coagulator" J Neurosurg, vol. 75, Jul. 1991, pp. 148-151.

* cited by examiner

ELECTROSURGICAL INSTRUMENT INCLUDING NESTED KNIFE ASSEMBLY

CROSS REFERENCE TO RELATED APPLICATION

The present application claims the benefit of and priority to U.S. Provisional Application Ser. No. 61/681,425, filed on Aug. 9, 2012, the entire contents of which are incorporated herein by reference.

BACKGROUND

Technical Field

The present disclosure relates to an electrosurgical instrument and, more particularly, to a knife assembly configured for use with the electrosurgical instrument.

Description of Related Art

Electrosurgical forceps are well known in the medical arts. For example, electrosurgical endoscopic forceps are utilized in surgical procedures, e.g., laparoscopic surgical procedure, where access to tissue is accomplished through a cannula or other suitable device positioned in an opening on a patient. The endoscopic forceps, typically, include a housing, a handle assembly including a movable handle, a drive assembly, a shaft and an end effector assembly attached to a distal end of the shaft. Typically, the endoscopic forceps utilize both mechanical clamping action and electrical energy to effect hemostasis by heating the tissue and blood vessels to coagulate, cauterize, seal, cut, desiccate, and/or fulgurate tissue. In particular, the jaw members operably communicate with the drive assembly to manipulate tissue, e.g., grasp and seal tissue, and the jaw members have respective seal plates secured to the jaw housing of the respective jaw members to seal tissue. Electrosurgical forceps typically include a knife assembly to cut tissue. To safely cut tissue, the user must be careful to avoid any inadvertent contact of tissue with the knife assembly prior to the cutting process.

SUMMARY

In view of the foregoing, a need exists for a knife assembly that can be positioned safely within the electrosurgical instrument to avoid inadvertent contact with tissue.

In accordance with an embodiment of the present disclosure, there is provided an electrosurgical instrument for sealing and/or cutting tissue. The instrument includes a handle assembly and an end effector assembly operatively coupled to the handle assembly. The end effector assembly includes a first jaw member including a first jaw housing and a first electrically conductive surface, a second jaw member including a second jaw housing and a second electrically conductive surface, and a knife assembly. The first and second jaw members are movable relative to the other between a first position in which the first and second jaw members are disposed in spaced apart relation relative to one another and a second position in which the first and second jaw members cooperate to grasp tissue therebetween. The knife assembly includes a base member translatably disposed in the first jaw housing, a pivot portion coupled with the base portion, and a blade pivotally associated with the pivot portion. In particular, the knife assembly is transitionable between a retracted state in which the blade is disposed within the first jaw housing and an extended state in which the blade is disposed at least partially within the second jaw housing.

In an embodiment, the blade of the knife assembly may include a blade edge configured to cut tissue. In particular, the blade edge may be oriented away from the electrically conductive sealing surfaces when the knife assembly is in the retracted state.

In another embodiment, the first jaw housing may include a slit configured to secure a portion of the blade therein. A portion of the blade may be secured within the slit in a friction fit engagement. In addition, the slit may define an opening substantially parallel to the second electrically conductive sealing surface. Moreover, the blade may be disposed entirely within the first jaw member when the blade is in the retracted state. The blade may extend from the first jaw member to the second jaw member when the blade is in the extended state.

In yet another embodiment, the pivot portion may include a plurality of circumferentially arranged and radially extending teeth corresponding to a plurality of circumferentially defined grooves in the base member. Each tooth may be configured to slidably engage each groove.

In still another embodiment, the end effector assembly may further include an actuation assembly including a helical gear and a worm gear operatively coupled with the base member of the knife assembly. The actuation assembly may be configured to cause translation of the knife assembly.

The end effector assembly may further include a plurality of sensors including a first sensor in the first jaw member, a second sensor in the second jaw member, and a third sensor in the blade to detect position and orientation of the blade prior to cutting tissue. In particular, the first sensor may be aligned with the third sensor when the blade is in the retracted state and the second sensor may be aligned with the third sensor when the blade is in the extended state.

In still yet another embodiment, at least one of the electrically conductive surfaces may define a channel extending along a length thereof. In particular, the channel may be configured for reciprocation of the blade therein.

In accordance with another embodiment of the present disclosure, there is provided an electrosurgical instrument for sealing and/or cutting tissue. The instrument includes a handle assembly and an end effector assembly operatively coupled to the handle assembly. The end effector assembly includes a first jaw member including a first jaw housing and a first electrically conductive surface, a second jaw member including a second jaw housing and a second electrically conductive surface, and a knife assembly. The first and second jaw members are movable relative to the other between a first position in which the first and second jaw members are disposed in spaced apart relation relative to one another and a second position in which the first and second jaw members cooperate to grasp tissue therebetween. The knife assembly includes a blade disposed within the first jaw housing. In particular, the blade is transitionable between a retracted state in which the blade is disposed entirely within the first jaw housing and an extended state in which the blade extends out of the first jaw housing and engages the second electrically conductive sealing surface of the second jaw member.

In an embodiment, the second electrically conductive sealing surface may include an anvil portion configured to engage the blade.

BRIEF DESCRIPTION OF THE DRAWINGS

Various embodiments of the present disclosure are described hereinbelow with references to the drawings, wherein.

DETAILED DESCRIPTION

Embodiments of the present disclosure are described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 1:
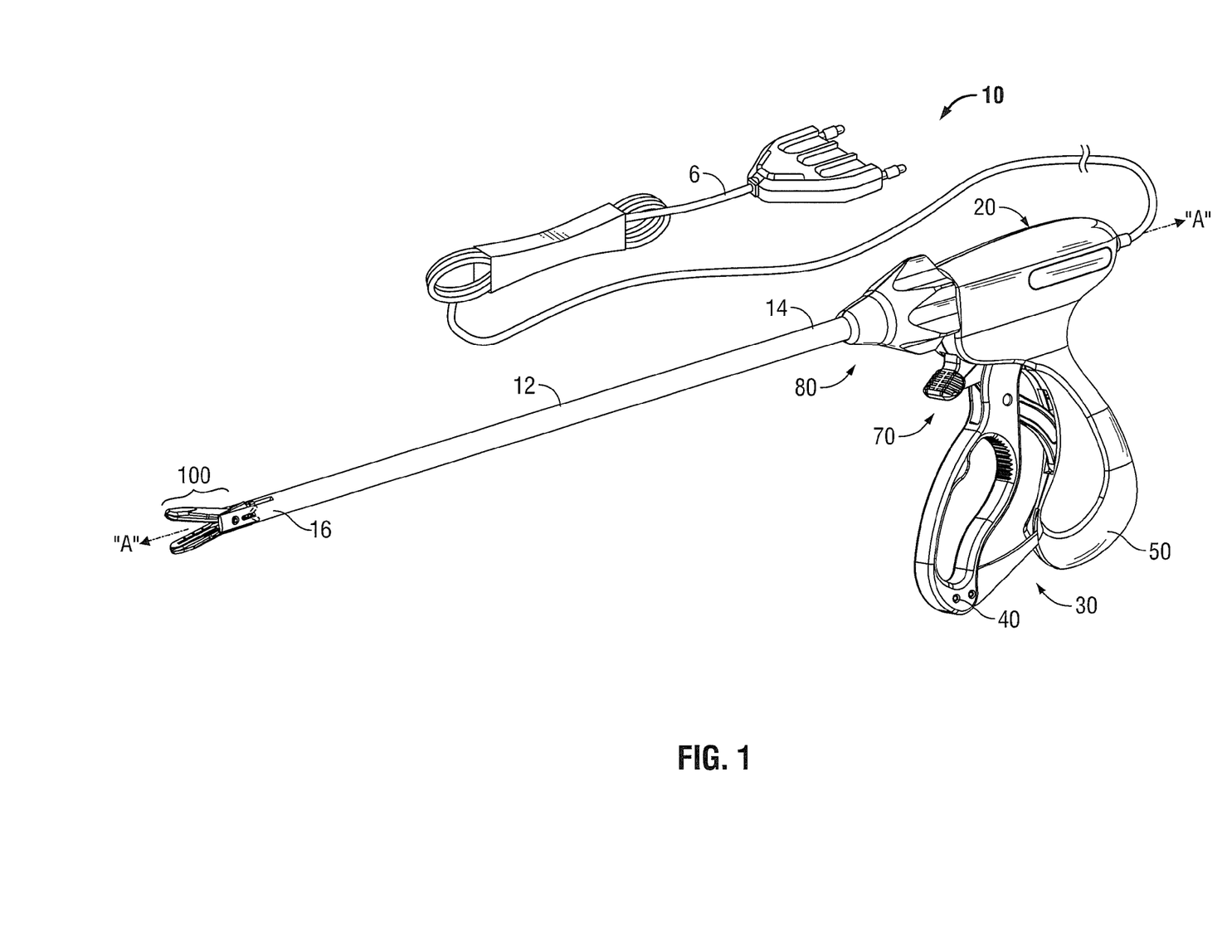
FIG. 1 is a perspective view of an endoscopic electrosurgical instrument including a knife assembly in accordance with an illustrative embodiment of the present disclosure.

With reference to FIG. 1, there is illustrated an endoscopic electrosurgical instrument 10 in accordance with an embodiment of the present disclosure. Instrument 10 includes a handle assembly 30, an elongated body 12 extending distally from handle assembly 30 and defining a longitudinal axis "A-A," and an end effector assembly 100 coupled to a distal end portion 16 of elongated body 12. End effector assembly 100 includes opposing jaw members 110, 120 (FIG. 2) that mutually cooperate to grasp, seal and divide tubular vessels and vascular tissue, as will be described in detail below. Instrument 10 also includes electrosurgical cable 6 that connects instrument 10 to a generator (not shown) or other suitable energy source. Alternatively, instrument 10 may be configured as a battery-powered instrument to facilitate an untethered operation. Cable 6 includes one or more wires (not shown) having sufficient length to extend through elongated body 12 in order to provide electrical energy to at least one of jaw members 110, 120 of end effector assembly 100.

With continued reference to FIG. 1, handle assembly 30 includes a housing 20, a switch assembly 70 configured to actuate a knife assembly 200 (FIG. 4), and a rotating assembly 80 configured to rotate with respect to housing 20 to selectively position end effector assembly 100 to any rotational orientation about longitudinal axis "A-A." Handle assembly 30 further includes a fixed handle 50 and a movable handle 40. Fixed handle 50 is integrally associated with housing 20 and movable handle 40 is movable relative to fixed handle 50 to actuate the opposing jaw members 110, 120 (FIG. 2) of end effector assembly 100. In particular, movable handle 40 imparts movement of jaw members 110, 120 about a pivot 160 (FIG. 2) from an open position in which jaw members 110, 120 are disposed in a spaced apart relation relative to one another to a clamping or closed position in which jaw members 110, 120 cooperate to grasp tissue therebetween.

Elongated body 12 has a proximal end 14 that mechanically engages housing 20. In particular, proximal end 14 of elongated body 12 mechanically engages rotating assembly 80 to facilitate rotation of end effector assembly 100 to any rotational orientation about longitudinal axis "A-A." Details relating to the mechanically cooperating components of elongated body 12 and rotating assembly 80 are described in commonly owned U.S. Patent Application Publication No. 2007/0260242, entitled "Vessel Sealer and Divider."

Figure 2:
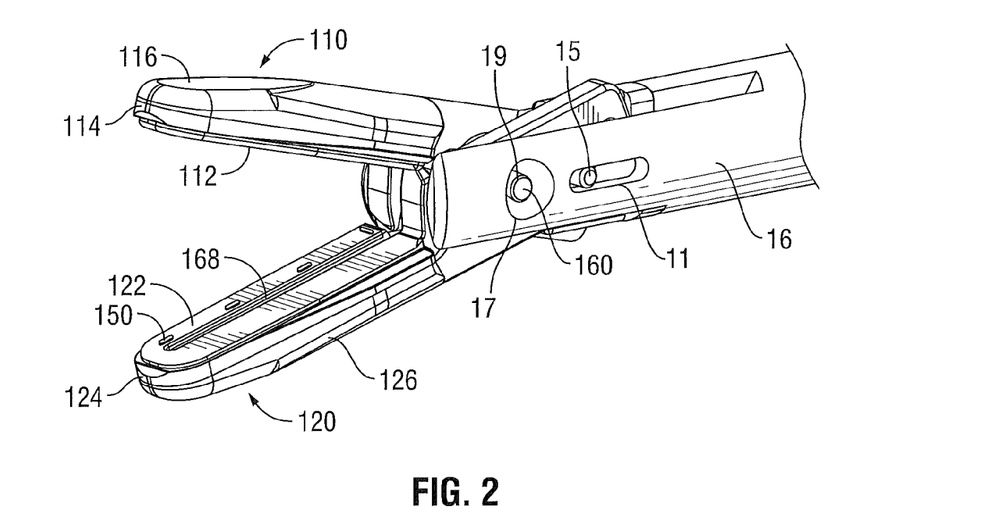
FIG. 2 is a partial, perspective view of the instrument of FIG. 1 illustrating jaw members of an end effector assembly in an open, spaced apart position.
Figure 3:
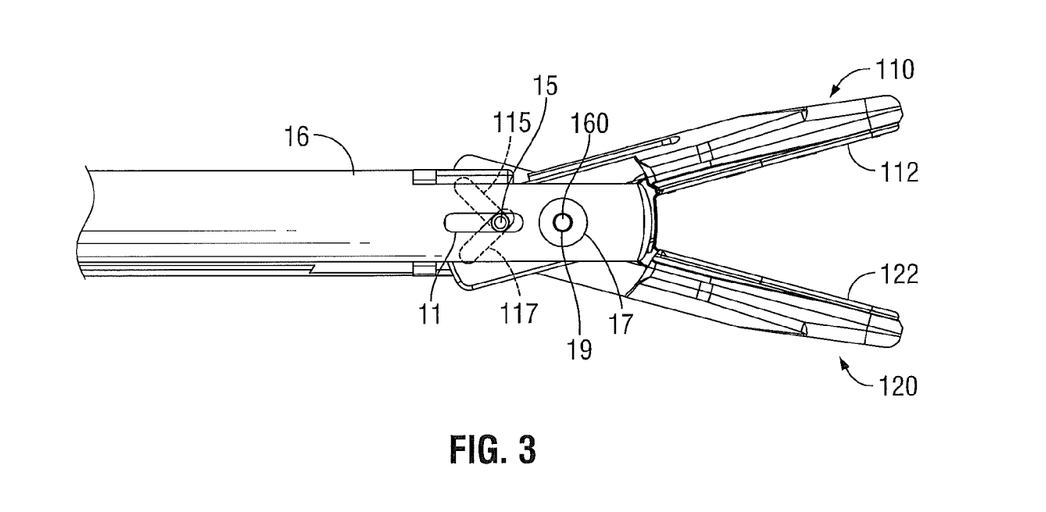
FIG. 3 is a partial, side view of the instrument of FIG. 2.

With reference to FIGS. 2 and 3, elongated body 12 may include one or more known mechanically engaging components that are designed to securely receive and engage end effector assembly 100 such that jaw members 110, 120 are pivotable relative to one another to engage and grasp tissue therebetween. In particular, distal end portion 16 of elongated body 12 defines a pair of camming slots 11 on lateral sides thereof (only one shown) configured to slidably receive a camming pin 15 therein. In addition, distal end portion 16 of elongated body 12 further defines a pivot bore 17 configured to receive a pivot pin 19 to pivotally couple jaw members 110, 120 about pivot 160. Jaw members 110, 120 define camming slots 115, 117 (shown in phantom in FIG. 3), respectively. Camming slots 115, 117 are configured to slidably receive camming pin 15 therein. Each camming slot 115, 117 defines an acute angle with respect to longitudinal axis "A-A" (FIG. 1), whereby sliding movement of camming pin 15 within camming slots 11, 115, 117 pivotally moves jaw members 110, 120 between the open or spaced apart position and the closed or clamping position about pivot 160.

With continued reference to FIGS. 2 and 3, jaw members 110, 120 are generally symmetrical and include similar component features, which cooperate to permit facile rotation about pivot 160 to effect sealing and dividing of tissue. Jaw member 110 includes a jaw housing 116 coated with an insulative coating 114 to reduce stray current concentrations during sealing and an electrically conductive sealing surface 112. However, in some embodiments, jaw housing 116 may include an insulative substrate or insulator configured to securely engage electrically conductive sealing surface 112. This may be accomplished by stamping, by overmolding, by overmolding a stamped electrically conductive sealing plate and/or by overmolding a metal injection molded seal plate. All of these manufacturing techniques produce an electrode having an electrically conductive sealing surface that is substantially surrounded by an insulating substrate. In certain instances, it may prove advantageous to provide an exterior portion of jaw housing 116 that is made from metal and an interior portion (e.g., a portion that is configured to support a seal plate thereon) of jaw housing 116 that is made from plastic. In this instance, the interior portion serves as an insulative barrier between the seal plate and the exterior portion of jaw housing 116.

Similarly, jaw member 120 includes a jaw housing 126 coated with an insulative coating 124 to reduce stray current concentrations during sealing and an electrically conductive sealing surface 122. However, in some embodiments, jaw housing 126 may include an insulator and an electrically conductive sealing surface that is dimensioned to securely engage the insulator. Electrically conductive sealing surface 122 defines a longitudinally-oriented channel 168 configured to receive a blade 230 (FIG. 4) therethrough. Channel 168 facilitates longitudinal reciprocation of blade 230 along a preferred cutting plane to effectively and accurately separate tissue along the formed tissue seal. Although not shown, jaw member 110 may also define a knife channel that cooperates with channel 168 to facilitate translation of blade 230 through tissue.

Jaw members 110, 120 are electrically isolated from one another such that electrosurgical energy can be effectively transferred through tissue to form a tissue seal. Electrically conductive sealing surfaces 112, 122 are also isolated from the remaining operative components of end effector assembly 100 and elongated body 12. A plurality of stop members 150 are employed to regulate the gap distance between sealing surfaces 112, 122 to ensure accurate, consistent and reliable tissue seals. Gap distances within the range of about 0.001 inch to about 0.006 inch are known to produce quality seals.

Figure 4:
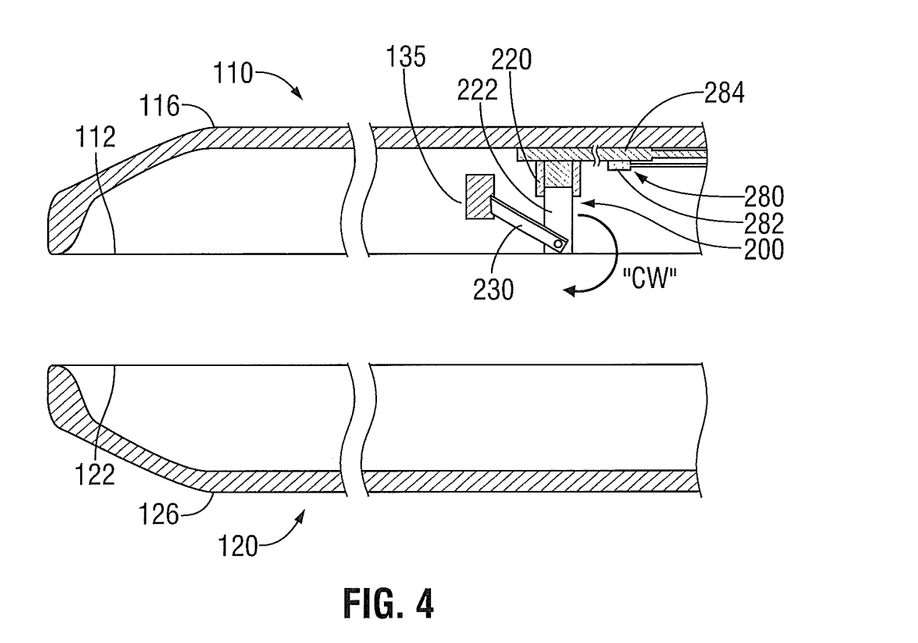
FIG. 4 is a partial, longitudinal cross-sectional view of the end effector assembly of FIG. 2 illustrating the knife assembly in a retracted state.
Figure 5:
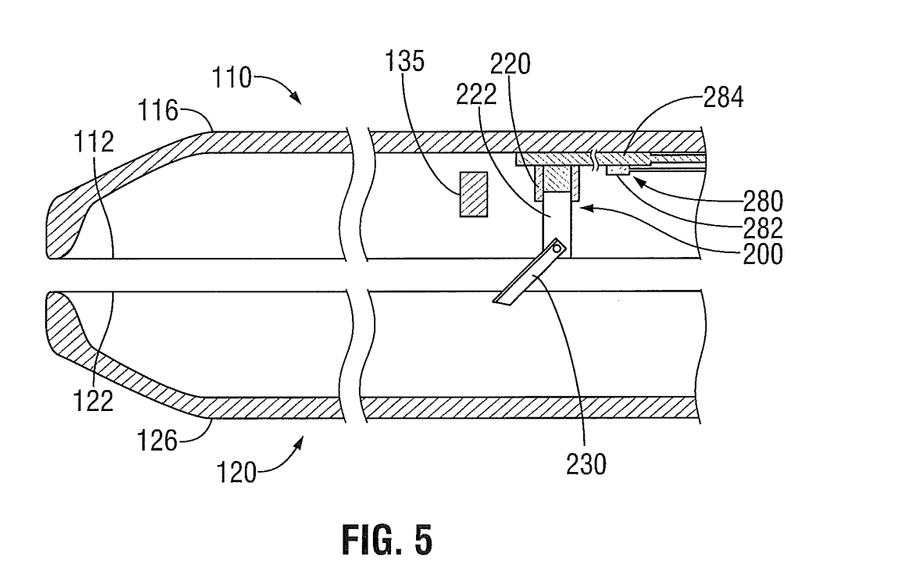
FIG. 5 is a partial, longitudinal cross-sectional view of the end effector assembly of FIG. 4 illustrating the knife assembly in an extended state.

With reference now to FIGS. 4 and 5, end effector assembly 100 includes a knife assembly 200 configured to cut tissue prior to and/or subsequent to the sealing of tissue in accordance with an embodiment of the present disclosure. Knife assembly 200 includes a base portion 220, a blade 230, and a pivot portion 222 that supports blade 230. Blade 230 is pivotable between a retracted state (FIG. 4) which enables blade 230 to be disposed entirely within jaw housing 116 and an extended state (FIG. 5) which enables blade 230 to be disposed at least partially within jaw housing 126. In the retracted state (FIG. 4), blade 230 engages a slit (e.g., friction fit engagement) 135 to secure blade 230 therein. In the extended state (FIG. 5), blade 230 extends from jaw housing 116 into channel 168 (FIG. 2) defined in sealing surface 122.

Figure 6:
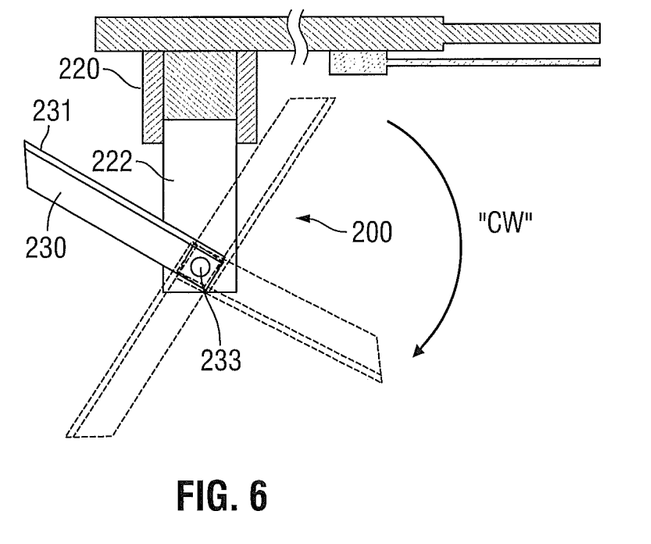
FIG. 6 is a side, cross-sectional view of the knife assembly of FIG. 4 illustrating pivotal movement of a blade of the knife assembly.
Figure 7:
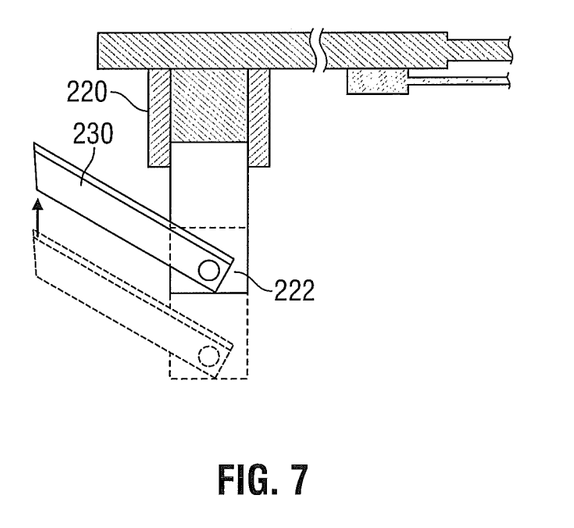
FIG. 7 is a side, cross-sectional view of the knife assembly of FIG. 6 illustrating transition of a pivot portion of the knife assembly between a retracted position and an extended position.
Figure 8:
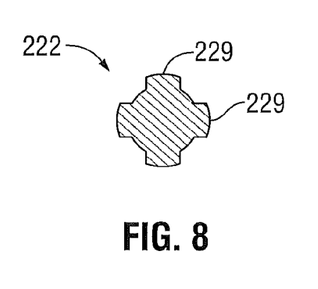
FIG. 8 is a cross-sectional view of the pivot portion of the knife assembly of FIG. 4.
Figure 9:
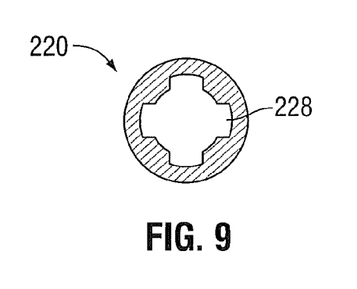
FIG. 9 is a cross-sectional view of a base portion of the knife assembly of FIG. 4.
Figure 10:
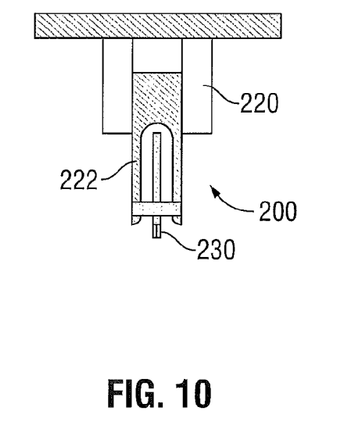
FIG. 10 is a front, cross-sectional view of the knife assembly of FIG. 7 in the retracted position.
Figure 11:
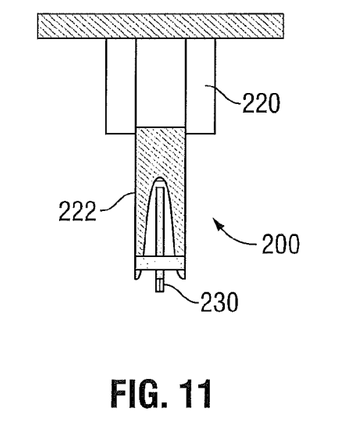
FIG. 11 is a front, cross-sectional view of the knife assembly of FIG. 10 in the extended position.

With reference to FIGS. 4-6, blade 230 is pivotally associated with pivot portion 222. When blade 230 is disposed in slit 135 of jaw housing 116 in friction fit engagement, a blade edge 231 (FIG. 6) is directed away (FIG. 4) from electrically conductive sealing surfaces 112, 122 or tissue (not shown) such that any inadvertent contact of tissue with blade edge 231 is avoided prior to cutting tissue. Knife assembly 200 may include a biasing member (not shown) such as, for example, a torsion spring, to bias blade 230 toward electrically conductive sealing surfaces 112, 122 or tissue when blade 230 is displaced from slit 135. Under such a configuration, upon disengagement of blade 230 from slit 135, blade 230 rotates about pivot point 233 in the direction of an arrow "CW" until blade edge 231 of blade 230 is oriented toward tissue (not shown) disposed between electrically conductive sealing surfaces 112, 122 (FIG. 5). In an embodiment, knife assembly 200 may also include a locking mechanism (not shown) that locks/maintains blade 230 in the extended state to facilitate consistent cutting of tissue.

In another embodiment, jaw housing 116 of jaw member 110 may further include an engaging portion (not shown) disposed adjacent slit 135. Initially, blade 230 is at least partially secured with slit 135 in jaw housing 116. However, upon distal translation of knife assembly 200, blade 230 contacts the engaging portion, which pushes blade 230 out of slit 135. The biasing member (not shown) urges blade 230 toward tissue by pivoting blade 230 in the direction of arrow "CW."

With reference to FIGS. 7-11, pivot portion 222 is slidably adjustable with respect to base portion 220. Such a configuration enables the clinician to adjust placement of blade 230 between sealing surfaces 112, 122 based on, for example, the thickness of tissue (not shown). In order to facilitate sliding movement of pivot portion 222 with respect to base portion 220 without causing misalignment with channel 168, pivot portion 222 includes a plurality of circumferentially arranged and radially extending teeth 229. Base portion 220 defines a plurality of circumferentially arranged grooves 228 configured to receive respective teeth 229 of pivot portion 222 therein. In this manner, pivot portion 222 may be slidably secured at least partially within base portion 220, while inhibiting rotation of pivot portion 222 with respect to base portion 220.

In an embodiment, jaw members 110, 120, as well as blade 230 may further include sensors (not shown) to determine the position and orientation of blade 230 in the extended and retracted states. When blade 230 is properly secured in slit 135, sensors on blade 230 and jaw member 110 may be properly aligned. Similarly, when blade 230 is properly positioned in channel 168 of jaw member 120, sensors on blade 230 and jaw member 120 may be properly aligned. The sensors may employ, for example, mechanical, optical, magnetic or electrical means. The data collected by the sensors may be sent to a user in a relatively remote location through, for example, wireless means (not shown). Additionally, the sensors may be placed in offset/misaligned positions to detect improper position or orientation of blade 230 in the retracted and extended states.

With reference back to FIGS. 4 and 5, knife assembly 200 is operatively coupled with an actuation assembly 280. In particular, actuation assembly 280 includes a helical gear 282 and a worm gear 284 rotatably coupled with helical gear 282. Rotation of helical gear 282 through a use of, e.g., a motor (not shown), causes translation of knife assembly 200 along channel 168 defined in electrically conductive sealing surface 122, which in turn enables cutting of tissue. In this manner, actuation of switch assembly 70 causes rotation of helical gear 282 which in turn enables cutting of tissue. It is contemplated that other gear combinations such as, for example, rack and pinion, or any other gear may be used in knife assembly 200. Alternatively, switch assembly 70 may be mechanically coupled to base portion 220 such that actuation of switch assembly 70 causes translation of base portion 220 without actuation assembly 280 and a motor.

In use, the user initially energizes the opposing electrically conductive sealing surfaces 112, 122 to effectively seal tissue disposed between jaw members 110, 120. Once tissue is sealed or otherwise treated, actuation assembly 280 may be actuated to initiate the cutting process by knife assembly 200. Initially, blade 230 is in the retracted state. However, upon initiation of actuation assembly 280, blade 230 disengages slit 135 and is rotated to be positioned in channel 168 of jaw member 120. At this time, the user may translate knife assembly 200 distally to cut tissue through actuation of actuation assembly 280.

Figure 12:
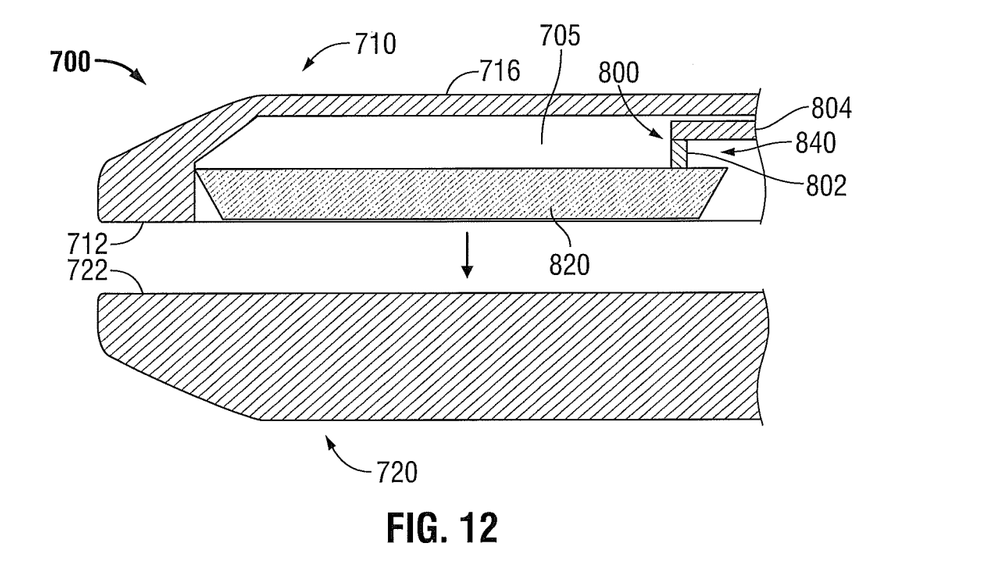
FIG. 12 is a partial, longitudinal cross-sectional view of an end effector assembly for use with the endoscopic electrosurgical instrument of FIG. 1 in accordance with another illustrative embodiment of the present disclosure.
Figure 13:
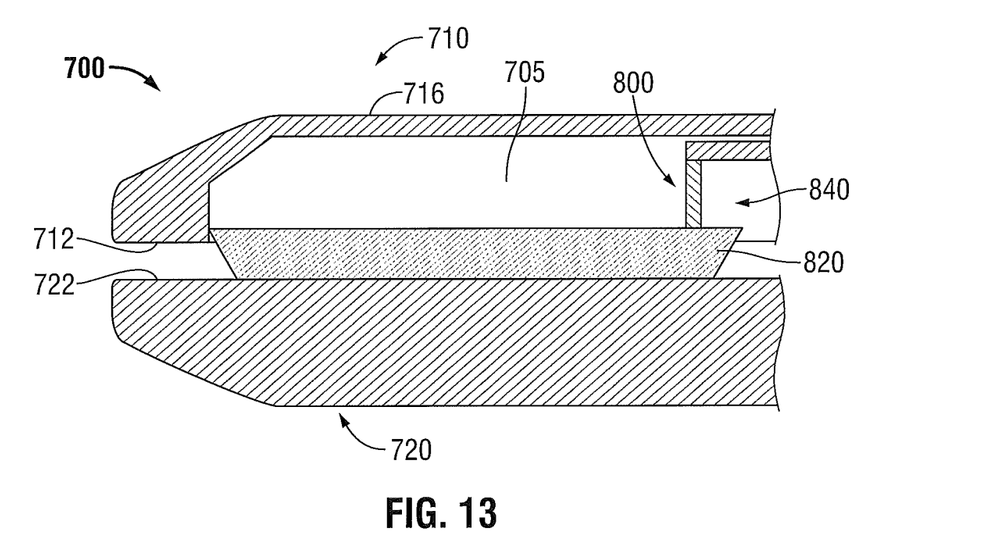
FIG. 13 is a partial, longitudinal cross-sectional view of the end effector of FIG. 12 illustrating a knife assembly in an extended state.

With reference now to FIGS. 12 and 13, an end effector assembly in accordance with another embodiment of the present disclosure is shown generally as 700. End effector assembly 700 includes pair of jaw members 710, 720 pivotally associated with each other to effect sealing and dividing of tissue. In particular, a jaw housing 716 of jaw member 710 includes a cavity 705 configured to receive a knife assembly 800 therein. Knife assembly 800 includes a knife member 820 movable between a retracted state (FIG. 12) and an extended state (FIG. 13). In the retracted state, knife member 820 is disposed entirely within cavity 705 of jaw member 710. In the extended state, knife member 820 extends out of jaw member 710 and engages an anvil portion (not shown) of electrically conductive sealing surface 722 of jaw member 720 to cut tissue (not shown) disposed between electrically conductive sealing surfaces 712, 722.

Jaw housing 716 further includes a linear actuation assembly 840 including a rack 802 coupled with knife member 820 and a pinion 804 operatively coupled with a motor (not shown). Rotation of pinion 804 through a use of the motor causes translation of rack 802, which, in turn, causes translation of knife member 820 between the retracted and extended states. The motor may be operatively coupled with switch assembly 70, whereby actuation of switch assembly 70 causes rotation of pinion 804, which, in turn, enables cutting of tissue through translation of knife member 820 to the extended state. Other gear types or gear combinations such as, for example, worm gear, helical gear, and bevel gear, may be utilized to actuate knife member 820.

While several embodiments of the disclosure have been shown in the drawings, it is not intended that the disclosure be limited thereto, as it is intended that the disclosure be as broad in scope as the art will allow and that the specification be read likewise. In addition, while the illustrative embodiments have been shown with endoscopic instruments, the embodiments of the present disclosure may be used in open surgery instruments. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument for sealing and/or cutting tissue comprising:
    a handle assembly; and
    an end effector assembly operatively coupled to the handle assembly, the end effector assembly including:
        a first jaw member including a first jaw housing and a first electrically conductive surface;
        a second jaw member including a second jaw housing and a second electrically conductive surface, the first and second jaw members movable relative to each other between a first position in which the first and second jaw members are disposed in spaced apart relation relative to one another and a second position in which the first and second jaw members cooperate to grasp tissue therebetween; and
        a knife assembly including:
            a blade disposed within the first jaw housing, the blade transitionable between a retracted state in which the blade is disposed entirely within the first jaw housing and an extended state in which the blade linearly extends out of the first jaw housing in a direction perpendicular to the first electrically conductive surface and engages the second electrically conductive surface of the second jaw member.

2. The electrosurgical instrument according to claim 1, wherein the second electrically conductive surface includes an anvil portion configured to engage the blade.

3. The electrosurgical instrument of claim 1, wherein the knife assembly further includes:
    a rack operatively coupled to the blade; and
    a pinion operatively coupled to the rack,
    wherein rotation of the pinion causes the rack to translate thereby causing the blade to extend out of the first jaw housing.

* * * * *